United States Patent
Wang et al.

(10) Patent No.: US 9,339,587 B2
(45) Date of Patent: May 17, 2016

(54) COMPOSITION AND METHODS FOR REPAIR OF CONNECTIVE TISSUE

(75) Inventors: Hali Wang, The Hills, TX (US); Jian Q. Yao, Shanghai (CN)

(73) Assignee: Zimmer Orthobiologics, Inc., Austin, TX (US)

( * ) Notice: Subject to any disclaimer, the term of this patent is extended or adjusted under 35 U.S.C. 154(b) by 1326 days.

(21) Appl. No.: 12/736,314

(22) PCT Filed: Dec. 22, 2008

(86) PCT No.: PCT/US2008/088041
§ 371 (c)(1),
(2), (4) Date: Dec. 13, 2010

(87) PCT Pub. No.: WO2009/086313
PCT Pub. Date: Jul. 9, 2009

(65) Prior Publication Data
US 2011/0111028 A1    May 12, 2011

Related U.S. Application Data

(60) Provisional application No. 61/124,814, filed on Dec. 20, 2007.

(51) Int. Cl.
```
A61P 19/04    (2006.01)
A61K 38/39    (2006.01)
A61K 47/42    (2006.01)
A61K 9/14     (2006.01)
A61L 27/24    (2006.01)
A61L 27/52    (2006.01)
A61L 27/54    (2006.01)
```

(52) U.S. Cl.
CPC ............... *A61L 27/24* (2013.01); *A61L 27/52* (2013.01); *A61L 27/54* (2013.01); *A61L 2300/414* (2013.01)

(58) Field of Classification Search
CPC ......... A61L 27/24; A61L 27/52; A61L 27/54; A61L 2430/00; A61L 2300/414
USPC ........... 424/484; 514/17.1, 17.2, 8.1, 8.2, 8.9, 514/9.1
See application file for complete search history.

(56) References Cited

U.S. PATENT DOCUMENTS 4,772,288 A    9/1988  Borner et al.
6,592,623 B1   7/2003  Bowlin et al.
2003/0194397 A1  10/2003  Mishra
2007/0005139 A1   1/2007  Vacanti et al.
2008/0166421 A1   7/2008  Buhr

FOREIGN PATENT DOCUMENTS

| CA | 2 285 161 A1 | | 4/2001 |
|---|---|---|---|
| CA | 2 285 161 | * | 6/2001 |
| WO | WO 85/00511 A1 | | 2/1985 |
| WO | WO 00/69355 A1 | | 11/2000 |
| WO | WO 2004/029230 | * | 4/2004 |
| WO | WO 2004/029230 A2 | | 4/2004 |

OTHER PUBLICATIONS

Provencher et al. (Mar. 2007) Techniques in Orthopaedics, vol. 22(1), 43-54.*
Liao et al. (Mar., 2007) Tissue Engineering, vol. 13(3), 537-550.*
Definition of "adjacent" from the online Merriam-Webster Dictionary http://www.merriam-webster.com/dictionary/adjacent).*
Definition of "adjacent" from the online Macmillan Dictionary http://www.macmillandictionary.com/us/dictionary/american/adjacent).*
PCT/US2008/087016 International Preliminary Report on Patentability, Jul. 2010.
"International Application Serial No. PCT/US2008/087016, International Search Report mailed Sep. 2, 2010", 5 pgs.
"International Application Serial No. PCT/US2008/087016, Written Opinion mailed Jun. 20, 2010", 6 pgs.
"International Application Serial No. PCT/US2008/088041, Preliminary Report on Patentability mailed Jun. 22, 2010", 8 pgs.
"International Application Serial No. PCT/US2008/088041, Search Report mailed Sep. 2, 2010", 5 pgs.
"International Application Serial No. PCT/US2008/088041, Written Opinion mailed Jun. 20, 2010", 7 pgs.

* cited by examiner

*Primary Examiner* — Anne Marie S Wehbe
(74) *Attorney, Agent, or Firm* — Schwegman Lundberg & Woessner, P.A.

(57) ABSTRACT

Compositions and methods for repairing a ruptured connective tissue are disclosed. The composition may include a first biocompatible material to provide a scaffold for connective tissue cell growth and tissue repair. This first biocompatible material may withstand a tensile load of up to 250 N. The composition may also include a second biocompatible material including at least one bioactive agent that can stimulate connective tissue cell growth and tissue repair. The method may include positioning a first end of the first biocompatible material adjacent a first end of a ruptured connective tissue, positioning a second end of the first biocompatible material adjacent a second end of the ruptured connective tissue, and anchoring the first biocompatible material to the first and second tendon ends. The method may alternatively comprise or further include positioning a second biocompatible material between the first and second ends of the ruptured connective tissue.

9 Claims, 3 Drawing Sheets

COMPOSITION AND METHODS FOR REPAIR OF CONNECTIVE TISSUE

This application is national stage entry of PCT/US2008/88041 filed On Dec. 22, 2008 which claims priority to United States provisional application 61/124,814 filed Dec. 20, 2007.

TECHNICAL FIELD

Medical compositions and methods, more particularly, medical compositions and methods for repair of ruptured tendons, ligaments, meniscus, and other connective tissues.

BACKGROUND

This section is intended to introduce the reader to various aspects of art that may be related to various aspects of the present invention, which are described and/or claimed below. This discussion is believed to be helpful in providing the reader with background information to facilitate a better understanding of various aspects of the present invention. Accordingly, it should be understood that these statements are to be read in this light, and not as admissions of prior art.

A tendon is a band of fibrous connective tissue that connects muscle to bone and is built to withstand tension. The tendon joins to a muscle at the origin of the tendon. There, collagen fibers from the muscle are continuous with those of the tendon. The tendon inserts into a bone at an enthesis where the collagen fibers are mineralized and integrated into the bone tissue. Tendons transfer the contractions of muscles and can exert an elastic force if stretched.

The Achilles tendon (also known as the calcaneal tendon) is a tendon of the posterior leg. It serves to attach the calf muscles (lateral and medial gastrocnemius muscle and soleus muscle) and the plantaris muscle to the heel bone (calcaneus).

The rotator cuff includes a group of tendons (supraspinatus, infraspinatus, teres minor, and subscapularis). This group of tendons and muscles in the rotator cuff connect the humerus (arm) with the scapula (shoulder blade).

Injury to a tendon can occur when the tensile load applied to the tendon exceeds its loadbearing capacity, causing the tendon to rupture. For example, rupture of the Achilles tendon is an injury that commonly occurs in males during sporting activities, generally as an acceleration injury (e.g., pushing off or jumping up). The diagnosis of an acute Achilles tendon rupture is usually straightforward. There is typically a snapping sensation and/or an audible snap in the posterior aspect of the ankle. The subject feels pain and is unable to bear weight due to both pain and weakness.

Treatment options for a ruptured tendon (such as a ruptured Achilles tendon or ruptured tendons in the rotator cuff) include conservative management, percutaneous repair, and open surgical repair. It is believed that open surgical repair provides the best chance for restoration of strength, power, and function of the muscle-tendon-bone complex with the lowest risk for repeat rupture. However, the management of a neglected Achilles tendon rupture poses certain problems to the surgeon as, by the time the subject is seen, the tendon ends have often retracted, forming a gap therebetween. Additionally, during surgery, the damaged tendon ends are debrided. Debridement may form a gap, and/or debridement may expand an already-existing gap. In order to treat the tendon to a full recovery, this gap must be closed. Various techniques have been used to eliminate this gap.

First, a surgeon can pull the two free tendon ends together and affix them to one another with sutures. However, when pulling the two free tendon ends together, each of the tendon ends is stretched. This weakens the tendon by decreasing the amount of tensile load the now-repaired tendon can withstand. This will cause functional deficiency of the tendon later, thereby increasing the likelihood of a repeat rupture.

Alternatively, portions of the Achilles tendon itself may be used to repair the tendon. For example, a strip of the superficial part of the tendinous portion of the proximal stump of the Achilles tendon may be used to augment repair. This is accomplished by making a posterior longitudinal incision and dissecting a half-inch by seven to nine-inch strip of tendon on a distal pedicle. The strip is then threaded through the trimmed ends of the ruptured tendon and sutured to them. However, this method also may not fully repair the tendon, as part of the tendon itself needs to be stripped away to repair the tendon.

Alternatively still, additional autologous tissue may be used to "bridge" the two tendon ends. For example, the tendon of the flexor hallucis longus (FHL) muscle of the leg has been used to bridge gaps in ruptured Achilles tendons. The FHL tendon is weaved through the ruptured Achilles tendon ends, and the distal end of the FHL tendon is adhered to the tendon of the flexor digitorum longus muscle of the second toe. Because the FHL tendon is a long tendon, it allows bridging of large Achilles tendon gaps. However, there are drawbacks to this treatment. For example, the process requires not only surgery to repair the ruptured Achilles tendon, but also to obtain the FHL tendon. Further, use of the FHL tendon impairs the normal function of the FHL tendon and FHL muscle. For example, in athletes, the loss of push-off from the toes (particularly the hallux) may cause difficulty when sprinting.

The tendon of the peroneus brevis muscle has also been used to bridge the gap of a ruptured Achilles tendon. The peroneus brevis tendon is harvested and passed through a transosseous drill hole formed in the heel bone. The peroneus brevis tendon is then passed back onto itself and sutured over the Achilles tendon. Like the use of the FHL tendon, above, use of the peroneus brevis tendon has drawbacks. For example, the normal function of the peroneus brevis tendon and peroneus brevis muscle is impaired.

Additionally, researchers have used human acellular dermal matrix grafts and porcine small intestinal submucosa for bridging tendon gaps in animals. However, these materials only provide a scaffold, but do not promote tendon cell growth and tissue repair to the degree of autologous tissue. Further, small intestinal submucosa can only withstand a small tensile load (approximately 40-50 N). This is much less than the tensile load capability of native tendon. This results in a weakened repaired tendon and the increased likelihood of repeat rupture.

In view of the drawbacks associated with current compositions and methods for tendon repair, a new and/or improved composition and method for repairing a ruptured tendon is desirable.

SUMMARY

Certain exemplary aspects of the invention are set forth below. It should be understood that these aspects are presented merely to provide the reader with a brief summary of certain forms the invention might take and that these aspects are not intended to limit the scope of the invention. Indeed, the invention may encompass a variety of aspects that may not be explicitly set forth below.

One aspect of the present invention provides a composition for bridging a gap in a ruptured tendon. In certain embodiments, the composition includes a first biocompatible material that can withstand a tensile load up to 250 N. The first biocompatible material is used to bridge a gap between a first end and a second end of a ruptured tendon. Thus, a first end of the first biocompatible material is associated with the first end of the ruptured tendon, such as by being sutured thereto, and a second end of the first biocompatible material is associated with the second end of the ruptured tendon, such as by being sutured thereto. The first biocompatible material thereby provides a scaffold in proximity to the gap for tendon cell growth and tissue repair. In various such embodiments, the first biocompatible material may comprise allograft tendon.

In other embodiments, the composition includes a first biocompatible material that provides a scaffold for tendon cell growth and tissue repair, and a second biocompatible material including at least one bioactive agent that can stimulate tendon cell growth and tissue repair. The first biocompatible material is used to bridge a gap between first and second ends of a ruptured tendon. Thus, a first end of the first biocompatible material is associated with the first end of the ruptured tendon, and a second end of the first biocompatible material is associated with the second end of the ruptured tendon. In various such embodiments, the first biocompatible material may comprise allograft tendon. The second biocompatible material may be positioned between the first and second ends of the ruptured tendon, and adjacent the first biocompatible material. As stated above, the second biocompatible material includes at least one bioactive agent (e.g., growth factors), which promotes cell growth and tissue repair. This enhances the repair abilities of the composition as compared to providing a scaffold alone. In various such embodiments, the second biocompatible material may comprise platelet rich plasma (PRP).

Another aspect of the present invention includes a method of repairing a ruptured tendon. In certain embodiments, the method includes positioning a first end of a first biocompatible material adjacent a first end of a ruptured tendon and positioning a second end of the first biocompatible material adjacent a second end of the ruptured tendon. The first biocompatible material may then be anchored to the first and second tendon ends, such as by sutures. In various such embodiments, the first biocompatible material may comprise allograft tendon. In certain embodiments, the method may further generally comprise positioning a second biocompatible material between the first and second ends of the ruptured tendon. The second biocompatible material may also be anchored to the first and second tendon ends and/or to the first biocompatible material. In various such embodiments, the second biocompatible material may comprise platelet rich plasma (PRP). In this manner, the first biocompatible material is used to bridge the gap between the two tendon ends, while the second biocompatible material promotes tissue growth and healing within and/or adjacent the gap.

Another aspect of the present invention includes a kit comprising the first biocompatible material and/or the second biocompatible material, each as previously described.

Another aspect of the present invention includes a method of repairing a ruptured tendon. In certain embodiments, the method includes delivering or applying a biocompatible material that includes at least one bioactive agent (e.g., growth factors), hereinbefore generally referred to as second biocompatible material, which promotes cell growth and tissue repair. In various such embodiments, platelet rich plasma (PRP) is delivered or applied to the subject tendon.

Various features discussed below in relation to one or more of the exemplary embodiments may be incorporated into any of the above-described aspects of the present invention alone or in any combination. Again, the brief summary presented above is intended only to familiarize the reader with certain aspects and contexts of the present invention without limitation to the claimed subject matter.

BRIEF DESCRIPTION OF THE DRAWINGS

The accompanying drawings, which are incorporated in and constitute a part of this specification, illustrate exemplary embodiments of the invention and, together with the summary given above, and the detailed description given below, serve to explain the invention.

DETAILED DESCRIPTION

Figure 1:
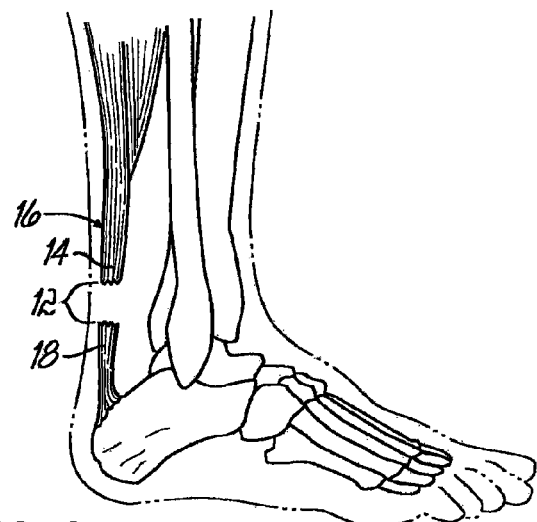
FIG. 1 is a perspective view of a ruptured Achilles tendon.

One or more specific embodiments of the present invention will be described below. In an effort to provide a concise description of these embodiments, not all features of an actual implementation may be described in the specification. It should be appreciated that in the development of any such actual implementation, as in any engineering or design project, numerous implementation specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present invention is generally directed to compositions for use in repairing connective tissue, such as ruptured connective tissue, and to the methods of repair. The present invention is applicable to the repair of various connective tissues, including tendons, ligaments, and meniscus. For ease of reference, the present invention is discussed below in the context of repairing a tendon, such as an Achilles tendon. One aspect of the present invention provides a composition for bridging a gap in a ruptured tendon. Referring to the Figures, in one embodiment, the present invention provides a composition that includes a first biocompatible material 10 that can withstand a tensile load up to 250 N. The first biocompatible material 10 is used to bridge a gap 12 between a first end 14 and a second end 18 of a ruptured tendon 16. Thus, a first end 20 of the first biocompatible material 10 is associated with the first end 14 of the ruptured tendon 16, and a second end 22 of the first biocompatible material 10 is associated with the second end 18 of the ruptured tendon 16. The first biocompatible material 10 thereby provides a scaffold in proximity to the gap 12 for tendon cell growth and tissue repair.

The first biocompatible material 10 may be substantially nonimmunogenic. Thus, it can be implanted into a subject with minimal chance of provoking an immune response. To achieve this, the first biocompatible material 10 may be acellular. Thus, in various embodiments, the first biocompatible material 10 includes a material or materials that are substantially nonimmunogenic, such as a material chosen from collagen and elastin. In further embodiments, the first biocompatible material 10 may include both collagen and elastin. However, it will be recognized by those skilled in the art that collagen and/or elastin are merely examples of such materials, and any other substantially nonimmunogenic materials suitable for the composition may be used. For example, such other substantially nonimmunogenic materials may include reconstituted collagen from human or animal sources, and/or may be synthetic, such as Sport Mesh, commercially available from Biomet, Inc. of Warsaw, Ind.

Further, the first biocompatible material 10 may be subjected to a process or processes to make it resistant to degradation, such as by enzymes (e.g., collagenase). To that end, in certain embodiments, the first biocompatible material 10 may be cross-linked. Such processes are known to those skilled in the art, and exemplary processes may include, but are not limited to, chemical cross-linking and photofixation. Exemplary processes are described in U.S. Pat. Nos. 5,397,353; 5,147,514; 5,332,475; 5,817,153, and/or 5,854,397, the disclosures of which is incorporated by reference herein in their entirety. However, other processes know to those of ordinary skill in the art may be used.

The first biocompatible material 10 may be autogenic, allogenic, or xenogenic with respect to the recipient of the composition. In various embodiments, the first biocompatible material 10 may be xenogenic and includes porcine dermal tissue. In such embodiments, the first biocompatible material 10 particularly may be an acellular scaffold of collagen and elastin, derived from porcine dermal tissue that can be used as a biological implant. The material may be cross-linked through a process that makes it resistant to collagenase degradation. Such a process was described above with respect to U.S. Pat. Nos. 5,397,353; 5,147,514; 5,332,475; 5,817,153, and/or 5,854,397. Thus, the first biocompatible material 10 is resistant to degradation and enzymatic attack, and also experiences no sensitization, rejection, allogenicity, or inflammatory response once implanted into a subject. This first biocompatible material 10 is strong and durable, and is readily and consistently colonized by host tissue cells and blood vessels. This first biocompatible material 10 may be provided in sheet form, and can withstand a significantly larger tensile load than small intestinal submucosa (SIS) patches (which, as described above, can generally withstand a tensile load of 40-50 N). In various embodiments, the first biocompatible material 10 can withstand a minimum load of 150N, can preferably withstand a tensile load between 150N and 250N, and more preferably can withstand a tensile load of 200N to 250N. In various particular embodiments, the first biocompatible material 10 can withstand a tensile load of up to 250 N. The first biocompatible material 10 may also have a thickness between 0.5 mm and 2.0 mm. In various particular embodiments, the first biocompatible material 10 has a 1.5 mm thickness and preservation of the original collagen structure of the porcine dermal tissue. One suitable first biocompatible material 10 is the Zimmer® Collagen Repair Patch, commercially available from Zimmer, Inc.

In other embodiments, the composition generally includes a first biocompatible material 10 to provide a scaffold for tendon cell growth and tissue repair, and a second biocompatible material 24 including at least one bioactive agent that can stimulate tendon cell growth and tissue repair. Such a bioactive agent may include a growth factor or mixture of growth factors, cytokines, and/or small peptides. In various such embodiments, the second biocompatible material 24 may comprise protein rich plasma (PRP). The first biocompatible material 10 is used to bridge a gap 12 between first and second ends 14, 18 of a ruptured tendon 16. Thus, a first end 20 of the first biocompatible material 10 is associated with the first end 14 of the ruptured tendon 16, and a second end 22 of the first biocompatible material 10 is associated with the second end 18 of the ruptured tendon 16. The second biocompatible material 24 may be positioned between the first and second ends 14, 18 of the ruptured tendon 16, and adjacent the first biocompatible material 10. In various such embodiments, the second biocompatible material 24 may be secured to the first biocompatible material 10, the first and/or second ends 14, 18 of a ruptured tendon, or to both the first biocompatible material 10, the first and/or second ends 14, 18 of a ruptured tendon. As stated above, the second biocompatible material includes at least one bioactive agent (e.g., growth factors, cytokines, small peptides), which promotes cell growth and tissue repair. This enhances the repair abilities of the present composition over those of the prior art.

As above, the first biocompatible material 10 may be substantially nonimmunogenic to minimize the chance of provoking an immune response. Toward this end, the first biocompatible material 10 may be acellular. Thus, in various embodiments, the first biocompatible material 10 includes a material or materials that are substantially nonimmunogenic, such as a material chosen from collagen and elastin. In further embodiments, the first biocompatible material 10 may include both collagen and elastin. However, it will be recognized by those skilled in the art that collagen and/or elastin are merely examples of such materials, and any other substantially nonimmunogenic materials suitable for the composition may be used. For example, such other substantially nonimmunogenic materials may include reconstituted collagen from human or animal sources, and/or may be synthetic, such as Sport Mesh, commercially available from Biomet, Inc. of Warsaw, Ind.

Further, the first biocompatible material 10 may be subjected to a process or processes to make it resistant to degradation, such as by enzymes (e.g., collagenase). To that end, in certain embodiments, the first biocompatible material 10 may be cross-linked. Such processes are known to those skilled in the art, and one such process is described in U.S. Pat. Nos. 5,397,353, 5,147,514; 5,332,475; 5,817,153, and/or 5,854,397, the disclosures of which are incorporated by reference herein in their entireties.

Further still, the first biocompatible material 10 may be autogenic, allogenic, or xenogenic with respect to the recipient of the composition. In various embodiments, the first biocompatible material 10 may be xenogenic and includes porcine dermal tissue. In this embodiment, the first biocompatible material 10 particularly may be an acellular scaffold of collagen and elastin, derived from porcine dermal tissue that can be used as a biological implant. The material may be cross-linked through a process that makes it resistant to collagenase degradation. An exemplary process is described above with respect to U.S. Pat. No. 5,397,353, 5,147,514; 5,332,475; 5,817,153, and/or 5,854,397. Thus, the first biocompatible material 10 is resistant to degradation and enzymatic attack. It also may provoke limited or substantially no sensitization, rejection, allogenicity, or inflammatory response once implanted into a subject. The first biocompatible material 10 is strong and durable, and is readily and consistently colonized by host tissue cells and blood vessels. This first biocompatible material 10 may be provided in sheet form, and can withstand a significantly larger tensile load than small intestinal submucosa (SIS) patches (which, as described above, can withstand a tensile load of 40-50 N). In various embodiments, the first biocompatible material 10 can withstand a minimum load of 150N, can preferably withstand a tensile load between 150N and 250N, and more preferably can withstand a tensile load of 200N to 250N. In various particular embodiments, the first biocompatible material 10 can withstand a tensile load of up to 250 N, which may be afforded by the first biocompatible material 10 having a thickness between 0.5 mm and 2.0 mm. In various particular embodiments, the first biocompatible material includes a 1.5 mm thickness and preservation of the original collagen structure of the porcine dermal tissue. One such first biocompatible material 10 is the Zimmer® Collagen Repair Patch, commercially available from Zimmer, Inc.

In embodiments including both first and second biocompatible materials 10, 24, the second biocompatible material 24 includes at least one bioactive agent that can stimulate tendon cell growth and tissue repair. Thus, in various embodiments, the second biocompatible material 24 may include, but is not limited to, at least one of platelet rich plasma (PRP), a collagen-based material, or a hydrogel. Each of these exemplary biocompatible materials may inherently include at least one bioactive agent (e.g., growth factors inherently present in PRP), or at least one bioactive agent may be incorporated into the material (e.g., growth factors added to a hydrogel, such that the hydrogel acts as a vehicle for the growth factors). In various particular embodiments, the second biocompatible material 24 comprises PRP, which may be autogenously harvested PRP. As is well known to those of ordinary skill in the art, PRP is a source of growth factors that support cell growth and soft tissue healing. It is derived by concentrating platelets and can be added to surgical wounds or grafts to support or speed up the healing process. PRP has previously been used in rotator cuff repair, bone healing, and to enhance ligament and meniscal repair in animals. (See Gamradt, Seth C. M.D.; Rodeo, Scott A. M.D.; and Warren, Russell F. M.D., in *Platelet Rich Plasma in Rotator Cuff Repair*, Techniques in Orthopaedics. Biologics in Shoulder Surgery. 22(1):26-33, March 2007; and Tomasz Mariusz Bielecki and Tadeusz Szymon Gazdzik, in *Percutaneous Injection Of Autogenous Growth Factors In Patient With Nonunion Of The Humerus. A Case Report*, J. Orthopaedics 2006; 3(3)e15.)

PRP includes multiple growth factors. Growth factors, as known to those of ordinary skill in the art, are naturally occurring proteins capable of stimulating cell proliferation and differentiation. PRP generally may include one or more of transforming growth factor (TGF), fibroblast growth factor (FGF), platelet-derived growth factor (PDGF), epidermal growth factor (EGF), and vascular endothelial growth factor (VEGF). TGFs present in PRP particularly include those of the TGF-β family. TGF-β is a protein that comes in three isoforms: TGF-β1, TGF-β2 and TGF-β3. The TGF-β family includes inhibins, activin, anti-mullerian hormone, bone morphogenetic protein, decapentaplegic and Vg-1. TGF-β controls proliferation, differentiation, and other functions of cells. It can also act as a negative autocrine growth factor.

FGFs are a family of growth factors involved in wound healing and embryonic development. The FGFs are heparin-binding proteins and interact with cell-surface associated heparan sulfate proteoglycans to assist in FGF signal transduction. FGF stimulates the proliferation of fibroblasts (a connective tissue cell) that give rise to granulation tissue, which fills up a wound space (i.e., the gap in a ruptured tendon) early in the wound healing process.

PDGF is a dimeric glycoprotein composed of two A or two B chains that regulates cell growth and division. In particular, it plays a role in blood vessel formation (angiogenesis), particularly the growth of blood vessels from already existing blood vessel tissue. Further, PDGF is an element in cellular division for fibroblasts.

EGF also plays a role in the regulation of cell growth, proliferation and differentiation. EGF acts by binding with high affinity to epidermal growth factor receptors (EGFR) on cell surfaces to stimulate the tyrosine kinase activity of the receptors. The tyrosine kinase activity in turn initiates a signal transduction cascade, which results in a variety of biochemical changes within the cell (e.g., increased intracellular calcium levels, increased glycolysis and protein synthesis, and increased expression of the gene for EGFR) that lead to DNA synthesis and cell proliferation.

VEGF is a signaling protein involved in angiogenesis. VEGF has been shown to stimulate endothelial cell mitogenesis and cell migration. VEGF is also a vasodilator and increases microvascular permeability.

Thus, the above growth factors in PRP may stimulate cell proliferation, differentiation, and migration at the site of the tendon gap, and stimulate the growth of blood vessels to supply nutrients to the tissue growth at the site of the tendon gap. This further promotes healing of the ruptured tendon.

Apart from the above growth factors, the second biocompatible material 24 comprising PRP may also have an additional component or components that aid in cell growth and tissue repair added to it. These may be additional growth factors, such as those listed and discussed above (so that the PRP has an enhanced concentration of its natural growth factors growth factors), or may be additional growth factors that are not inherently present in PRP. Alternatively, the additional component or components may be other than growth factors, for example, components having scaffold properties. In various embodiments, such a component is fibrin. As is known to those of ordinary skill in the art, fibrin is a protein that is polymerised to form a "mesh" that forms a hemostatic clot (in conjunction with platelets) over a wound site.

In alternate embodiments, the second biocompatible material 24 may be a material other than PRP. For example, the second biocompatible material 24 may comprise a hydrogel. Hydrogels are well known to those skilled in the art, and are a broad class of polymeric materials that swell extensively in water but do not dissolve in water. A hydrogel can be formed by polymerizing a hydrophilic monomer in an aqueous solution under conditions where the polymer becomes cross-linked, thus creating a three dimensional polymer network sufficient to gel the solution. Hydrogels are used extensively in biomaterials and have desirable properties. They can be made nontoxic and compatible with tissue, and they are usually highly permeable to water, ions and small molecules. When used as scaffolds, hydrogels may contain human cells in order to repair tissue. Common ingredients for hydrogels are, for example, polyvinyl alcohol, sodium polyacrylate, acrylate polymers and copolymers with an abundance of hydrophilic groups. Natural hydrogel materials have been and are being investigated for tissue engineering, and include agarose, methylcellulose, hylaronan, and other naturally derived polymers. Such hydrogels that may be used in embodiments of the present invention may have additional components added to them. Such components may include, but are not limited to, growth factors (such as TGF-β, FGF, PDGF, VEGF, and others) and fibrin, as discussed above.

Thus, the composition of the present invention can bridge a tendon gap 12 without taking or using any autologous tissues. It provides, for example, both a scaffold (the first biocompatible material 10) and growth factors (the second biocompatible material 24) to enhance tissue regeneration.

Another aspect of the present invention provides a kit comprising a the first biocompatible material 10 and/or a second biocompatible material 24, both as previously described.

Figure 2:
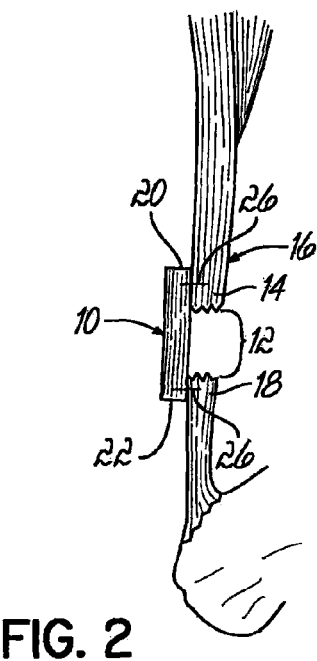
FIG. 2 is a perspective view of a first biocompatible material positioned adjacent a ruptured tendon.

Another aspect of the present invention provides a method of repairing or augmenting the repair of a ruptured tendon 16. FIG. 1 depicts a ruptured Achilles tendon 16 as exemplary tendon that may be repaired in accordance with the present invention. The tendon 16 includes a first end 14 and a second end 18. Referring now to FIG. 2, in one embodiment, the method includes positioning a first end 20 of a first biocompatible material 10 adjacent a first end 14 of a ruptured tendon 16, and positioning a second end 22 of the first biocompatible material 10 adjacent a second end 18 of the ruptured tendon 16. Thus, the first biocompatible material 10 provides a scaffold for tendon cell growth and tissue repair. This first biocompatible material 10 may withstand a tensile load of up to 250 N. Positioning the first end 20 and the second end 22 of the first biocompatible material 10 may further include anchoring the first end 20 of the first biocompatible material 10 to the first end 14 of the ruptured tendon 16, such as by the use of sutures 26, and/or anchoring the second end 22 of the first biocompatible material 10 to the second end 18 of the ruptured tendon 16, such as by the use of sutures 26. Those of ordinary skill in the art will recognize that sutures are not the only method of anchoring the first biocompatible material to a tendon, and that other methods suitable for the purposes of the present invention may be used. Such other methods include, but are not limited to, the use of staples and/or tacks.

Figure 3:
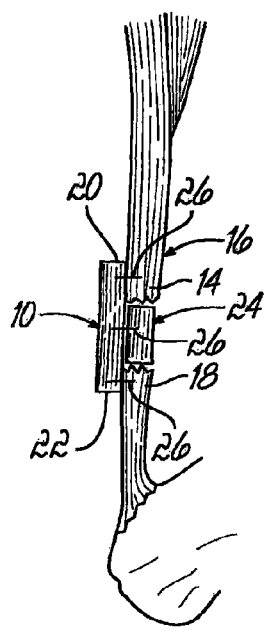
FIG. 3 is a perspective view of a first biocompatible material positioned adjacent a ruptured tendon and a second biocompatible material positioned adjacent and affixed to the first biocompatible material.
Figure 4:
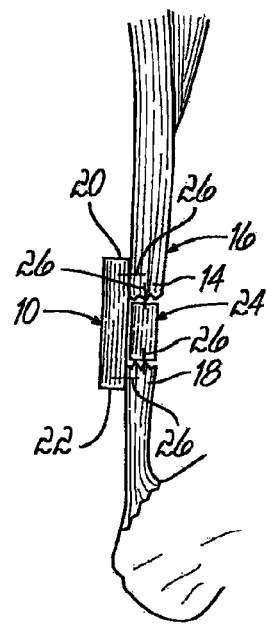
FIG. 4 is a perspective view of a first biocompatible material positioned adjacent a ruptured tendon and a second biocompatible material positioned adjacent and affixed to first and second ends of the ruptured tendon.
Figure 5:
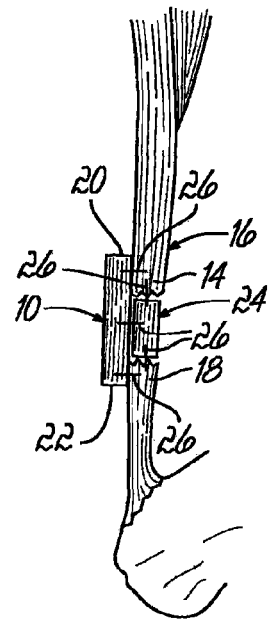
FIG. 5 is a perspective view of a first biocompatible material positioned adjacent a ruptured tendon and a second biocompatible material positioned adjacent and affixed to the first biocompatible material, and affixed to first and second ends of the ruptured tendon.
Figure 6:
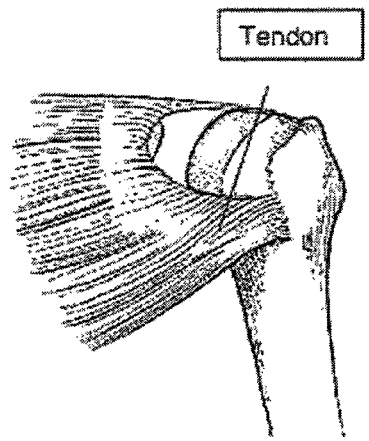
FIG. 6 is a perspective view of the tendons attaching to the humerus.
Figure 8:
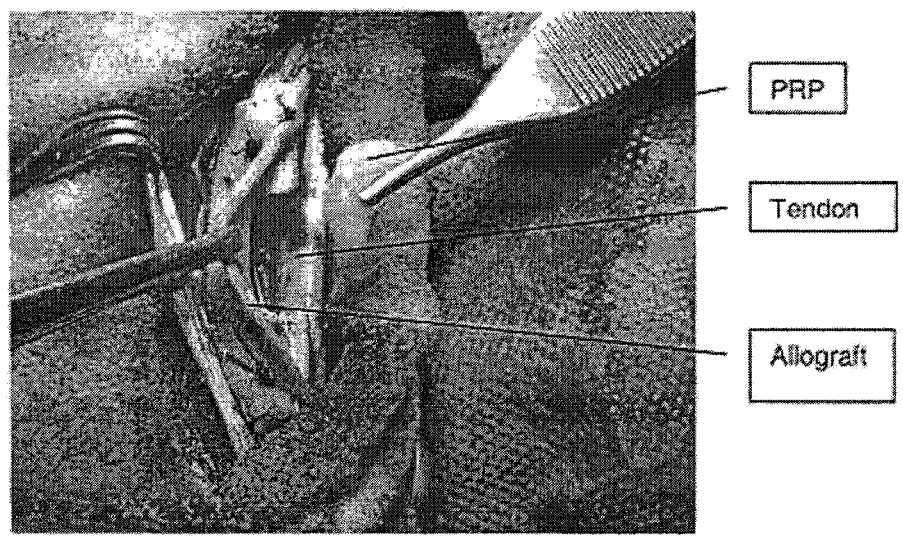
FIG. 8 is a photograph of a PRP placed under an allograft tendon.

The first biocompatible material 24 may be used by itself or the in various embodiments a second biocompatible material may be used. Referring to FIG. 3, a second biocompatible material 24 may be positioned between the first and second ends 14, 18 of the ruptured tendon 16. The second biocompatible material 24 may include at least one bioactive agent that can stimulate tendon cell growth and tissue repair. In particular, positioning the second biocompatible material 24 between the first and second ends 14, 18 of the ruptured tendon 16 may further include positioning the second biocompatible material 24 adjacent the first biocompatible material 10. Further still, and referring now to FIG. 5, positioning the second biocompatible material 24 adjacent the first biocompatible material 10 may include anchoring the second biocompatible material 24 to the first biocompatible material 10, such as by the use of sutures 26. Alternatively or additionally, the method may further include anchoring a first end of the second biocompatible material 24 to the first end 14 of the ruptured tendon 16 and/or anchoring a second end of the second biocompatible material 24 to the second end 18 of the ruptured tendon 16, such as by the use of sutures 26 (see FIG. 4). Those of ordinary skill in the art will recognize that sutures are not the only method of anchoring the second biocompatible material to the first biocompatible material, or to a tendon, and that other methods suitable for the purposes of the present invention may be used. Such other methods include, but are not limited to, the use of fibrin glue and/or a hydrogel. FIGS. 6 and 8 depict a scenario that is in accord with embodiments where both a first biocompatible material and second biocompatible material are employed. In FIG. 8, a method is depicted in which the defect gap in the ruptured tendon is bridged using allograft tendon as a scaffold. A PRP source is sutured under the scaffold allograft tendon to enhance healing and prevent re-rupture of the injured tendon.

In other embodiments, a method of repairing a ruptured tendon 16 may include positioning a first end 20 of a biocompatible material adjacent a first end 14 of a ruptured tendon 16, and positioning a second end 22 of the biocompatible material adjacent a second end 18 of the ruptured tendon 16. Again, the biocompatible material provides a scaffold for tendon cell growth and tissue repair, and the biocompatible material can withstand, in various particular embodiments, a tensile load up to 250 N. In various embodiments, the first biocompatible material 10 can withstand a minimum load of 150N, can preferably withstand a tensile load between 150N and 250N, and more preferably can withstand a tensile load of 200N to 250N.

The method may further include anchoring the first end 20 of the biocompatible material to the first end 14 of the ruptured tendon 16, and/or anchoring the second end 22 of the biocompatible material to the second end 18 of the ruptured tendon 16. Anchoring the first end 20 and the second end 22 of the biocompatible material may particularly include using sutures 26 to anchor the first end 20 of the biocompatible material to the first end 14 of the ruptured tendon 16, and using sutures 26 to anchor the second end 22 of the biocompatible material to the second end 18 of the ruptured tendon 16.

Figure 7:
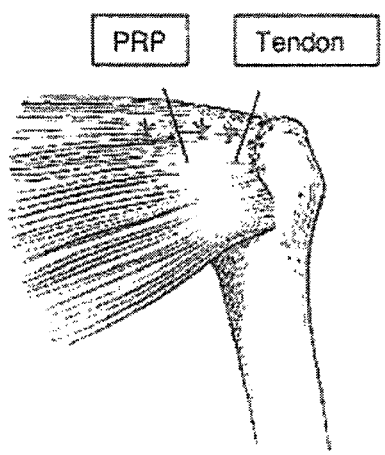
FIG. 7 is a perspective view of a Platelet Rich Plasma (PRP) which has been stutured below the tendons of the rotator cuff.

In other embodiments, the method includes delivering or applying a PRP to a tendon. The PRP source can be sutured under the tendon during normal tendon repair procedures using standard suturing techniques known in the art. See FIGS. 6 and 7. The PRP is preferably autogenic. As described above, PRP includes multiple growth factors. The PRP therefore acts as a growth factor resource for the injured tendon. Delivering or applying the PRP enhances tissue healing and prevents re-rupture of the tendon.

While the invention has been illustrated by the description of various embodiments, and while the various embodiments have been described in considerable detail, the inventors do not intend to restrict or in any way limit the scope of the appended claims to such detail. Additional advantages and modifications will readily appear to those skilled in the art. Moreover, the various features of the invention may be used alone or in numerous combinations depending on the needs and preferences of the user. Therefore, the invention in its broader aspects is not limited to the specific details, representative apparatus and methods, and illustrative examples shown and described. Accordingly, departures may be made from such details without departing from the scope or spirit of the general inventive concept.

The invention claimed is:

1. A connective tissue repair construct comprising:
    an acellular scaffold comprising collagen and elastin that is colonized by host tissue cells in vivo; and
    a hydrogel material comprising at least one bioactive agent that stimulates tendon cell growth and tissue repair,
    wherein the hydrogel material is positioned adjacent to the scaffold but does not surround the scaffold and the scaffold, or any portion thereof, does not surround the hydrogel material.

2. The connective tissue repair construct of claim 1, wherein the acellular scaffold is purified and cross-linked.

3. The connective tissue repair construct of claim 1, wherein the acellular scaffold can withstand a tensile load up to 250 N.

4. The connective tissue repair construct of claim 1, wherein the hydrogel material further comprises platelet rich plasma.

5. The connective tissue repair construct of claim 1, wherein the hydrogel material further comprises one or more growth factors selected from the group consisting of TGF-$\beta$, FGF, PDGF, EGF, VEGF, and combinations thereof.

6. A method of repairing a ruptured connective tissue, the method comprising: positioning a first end of an acellular scaffold adjacent a first end of a ruptured connective tissue; positioning a second end of the acellular scaffold adjacent a second end of the ruptured connective tissue; and positioning a hydrogel material between the first and second ends of the ruptured connective tissue; wherein:
   the acellular scaffold comprises collagen and elastin and is coloized by host tissue cells in vivo;
   the hydrogel material comprises at least one bioactive agent that stimulate cell growth and tissue repair; and
   the hydrogel material does not surround the scaffold and the scaffold, or any portion thereof, does not surround the hydrogel material.

7. The method of claim 6, wherein positioning the first end and the second end of the acellular scaffold further comprises anchoring the first end of the acellular scaffold to the first end of the ruptured connective tissue, and anchoring the second end of the acellular scaffold to the second end of the ruptured connective tissue.

8. The method of claim 6, wherein positioning the hydrogel material adjacent the first biocompatible material further comprises anchoring the hydrogel material to the acellular scaffold.

9. The method of claim 6, wherein the connective tissue is at least one of a tendon, a ligament, and a meniscus.

\* \* \* \* \*